(12) United States Patent
Wiktor

(10) Patent No.: US 11,246,968 B2
(45) Date of Patent: Feb. 15, 2022

(54) DIALYSIS MACHINE AND CONSTANT FLOW REGULATOR

(71) Applicant: FRESENIUS MEDICAL CARE DEUTSCHLAND GMBH, Bad Homburg (DE)

(72) Inventor: Christoph Wiktor, Gelnhausen (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 0 days.

(21) Appl. No.: 16/306,747

(22) PCT Filed: Jun. 2, 2017

(86) PCT No.: PCT/EP2017/000655
§ 371 (c)(1),
(2) Date: Dec. 3, 2018

(87) PCT Pub. No.: WO2017/207105
PCT Pub. Date: Dec. 7, 2017

(65) Prior Publication Data
US 2019/0125953 A1    May 2, 2019

(30) Foreign Application Priority Data
Jun. 3, 2016   (DE) .................... 10 2016 006 887.6

(51) Int. Cl.
*A61M 1/16*         (2006.01)
*F16K 17/30*        (2006.01)
(Continued)

(52) U.S. Cl.
CPC ........ *A61M 1/1656* (2013.01); *A61M 1/3413* (2013.01); *A61M 39/24* (2013.01);
(Continued)

(58) Field of Classification Search
CPC ......... A61M 1/1656; A61M 2039/2486; F16K 17/26; F16K 17/30; G05D 7/014;
(Continued)

(56) References Cited

U.S. PATENT DOCUMENTS 780,986 A * 1/1905 Francis ................ G05D 7/0133
137/504
3,105,477 A * 10/1963 Lowther .............. F01M 13/023
123/574
(Continued)

FOREIGN PATENT DOCUMENTS

| CH | 645070 | 9/1984 |
|----|--------|--------|
| CN | 1251642 | 4/2000 |

(Continued)

*Primary Examiner* — Reinaldo Sanchez-Medina
*Assistant Examiner* — Nicole Gardner
(74) *Attorney, Agent, or Firm* — Jacobson Holman PLLC

(57) ABSTRACT

A dialysis machine, in particular for hemodialysis and/or hemofiltration, having a dialyzate system and having a water inlet via which the dialyzate system can be connected to an external water supply. The dialysis machine includes a constant flow regulator that is arranged between the water connection and the dialyzate system.

18 Claims, 5 Drawing Sheets

(51) Int. Cl.
*G05D 7/01* (2006.01)
*F16K 17/26* (2006.01)
*A61M 1/34* (2006.01)
*A61M 39/24* (2006.01)

(52) U.S. Cl.
CPC .............. *F16K 17/26* (2013.01); *F16K 17/30* (2013.01); *G05D 7/0133* (2013.01); *A61M 2039/242* (2013.01); *A61M 2039/2486* (2013.01); *A61M 2205/3341* (2013.01)

(58) Field of Classification Search
CPC .. G05D 7/0133; G05D 16/028; G05D 16/103; G05D 16/101
See application file for complete search history.

(56) References Cited

U.S. PATENT DOCUMENTS

| | | | |
|---|---|---|---|
| 3,122,162 A | 2/1964 | Sands | |
| 3,359,960 A * | 12/1967 | Pittsley | F01M 13/023 123/574 |
| 3,431,944 A | 3/1969 | Sakuma | |
| 3,645,242 A * | 2/1972 | Horiuchi | F01M 13/023 123/574 |
| 3,659,573 A * | 5/1972 | Bennett | F01M 13/023 123/574 |
| 3,918,481 A * | 11/1975 | Doe | F16K 17/30 137/504 |
| 3,941,150 A * | 3/1976 | Anderson | A01G 25/023 137/504 |
| 4,510,993 A * | 4/1985 | Luetzelschwab | C09K 8/588 137/504 |
| 4,650,094 A * | 3/1987 | Werding | B65D 83/44 222/55 |
| 5,141,493 A * | 8/1992 | Jacobsen | A61M 1/1696 210/104 |
| 5,244,568 A * | 9/1993 | Lindsay | A61M 1/168 210/87 |
| 5,485,867 A | 1/1996 | Stoll | |
| 5,591,344 A * | 1/1997 | Kenley | A61L 2/04 210/636 |
| 6,019,115 A | 2/2000 | Sanders | |

FOREIGN PATENT DOCUMENTS

| | | |
|---|---|---|
| CN | 1465877 | 1/2004 |
| DE | 1003242 | 2/1957 |
| DE | 1648038 | 5/1971 |
| DE | 3342405 | 6/1985 |
| DE | 4317604 | 12/1994 |
| DE | 102009057562 | 6/2011 |
| EP | 1246036 | 10/2002 |
| EP | 1826649 | 8/2007 |
| EP | 2253352 | 11/2010 |
| EP | 2468390 | 6/2012 |
| JP | 60225573 | 11/1985 |
| JP | 61131753 | 6/1986 |
| JP | H0199566 | 4/1989 |
| JP | 2003290338 | 10/2003 |
| WO | WO 98/38555 | 9/1998 |
| WO | WO 20160/049542 | 3/2016 |

\* cited by examiner

DIALYSIS MACHINE AND CONSTANT FLOW REGULATOR

BACKGROUND OF THE INVENTION

1. Field of the Invention

The present invention relates in a first aspect to a dialysis machine having a dialyzate system and having a water inlet via which the dialyzate system can be connected to an external water supply. It is in particular a dialysis machine for hemodialysis and/or for hemofiltration.

2. Description of the Related Art

Such dialysis machines are typically connected to an ultrapure water supply at the installation site said water supply providing the dialyzate or permeate required for dialysis.

Since the pressure of the external water supply applied to the water inlet of the dialysis machine can fluctuate greatly from installation site to installation site, a pressure reducer is provided between the water connection and the dialyzate system in typical dialysis machines. FIG. 1 shows a basic diagram of such a dialysis machine in accordance with the prior art. The dialysis machine 1 has a water inlet 2 which can be connected to an external water supply and via which water can flow into an inlet chamber 3 of the dialyzate system. The pressure reducer 4 is provided in the line between the water inlet 2 and the inlet chamber 3 for adapting to different pressures of the external water supply. An inlet valve 5 is furthermore arranged in the line. On deployment at the installation site, the service engineer sets the inflow pressure into the inlet chamber of the dialyzate system to a desired value by means of the pressure reducer.

Such dialysis machines thus have the disadvantage that a service engineer is needed to set the pressure reducer at the installation site. Furthermore, no adaptation to fluctuating pressures during operation is provided. An optimum operating behavior is hereby not reached in all cases. Feed flows to the inlet chamber which are too low can in particular have the result that the dialysis machine does not achieve optimum performance. Feed flows which are too high in turn produce an additional load on the water supply.

SUMMARY OF THE INVENTION

It is therefore the object of the first aspect of the present invention to provide an improved dialysis machine.

In accordance with a second aspect, the present invention relates to a constant flow regulator.

A constant flow regulator is known from document EP 2 253 352 A1 which, as an implant, is intended to ensure a constant outflow of cerebrospinal fluid into other body openings with a hydrocephalus. The constant flow regulator known from this document has a housing which is flowed through by fluid and which comprises an inlet, a regulator opening and an outlet; a plunger is displaceably arranged in the housing, with a restrictor passage remaining between the regulator opening and the plunger which is dependent on the relative position between the plunger and the regulator opening and which defines the regulation effect. The regulator passage is fit into the periphery of the plunger in spiral form in EP 2 253 352 A1. If the plunger is displaced against the force of a spring by a differential pressure between the inlet and the outlet of the housing, the length of the regulator passage remaining between the regulator opening and the plunger changes. The constant flow regulator can produce a substantially constant volume flow over its operating pressure range by a corresponding setting of the spring force. The constant flow regulator known from EP 2 253 352 A1 is, however, only configured for low flow rates and can therefore not be used for dialysis machines.

A further regulator is known from WO 98/38555 A1. A needle-shaped plunger is used here which is displaced relative to a diaphragm in dependence on a differential pressure. The constant flow regulator of WO 98/38555 A1 is used in irrigation systems.

It is therefore the object of the second aspect of the present invention to provide an improved constant flow regulator. It should preferably be able to be used in a dialysis machine.

The above-named objects in accordance with the first and second aspects of the present invention are achieved by the independent claims of the present invention. Preferred embodiments of the invention form the subject of the dependent claims.

In accordance with the first aspect, the present invention comprises a dialysis machine having a dialysis system and having a water inlet via which the dialyzate system can be connected to an external water supply. The dialysis machine is in particular a machine for hemodialysis and/or for hemofiltration. Provision is made in accordance with the invention that a constant flow regulator is provided between the water connection and the dialyzate system. Such a constant flow regulator changes its flow resistance in dependence on the applied pressure difference such that an approximately constant flow independent of the pressure difference results over a predefined operating range.

The use of such a constant flow regulator in a dialysis machine has the advantage over the pressure reducers known from the prior art that the dialyzate system is reliably filled with a reproducible flow. A setting by the service engineer can furthermore be dispensed with since the desired flow can be predefined by the constant flow regulator. The constant flow regulator furthermore has the advantage that fluctuating pressures of the external water supply also have no influence on the flow at which the dialyzate system is filled. A dialysis machine in accordance with the invention can thus be connected to different external water supplies, for example to an ultrapure water line of different quality and load, to a single ultrapure water site, to a reverse osmosis plant, etc., without any setting by a service engineer.

It is furthermore ensured by the constant flow regulator that the dialysis machine in accordance with the invention reaches its optimum performance by the correct feed flow. Unnecessary loads on the water supply are furthermore prevented.

The dialyzate system of the dialysis machine in accordance with the invention can have a water inlet chamber which is filled with water by the external water supply. In this case, the constant flow regulator is preferably arranged between the water inlet of the dialysis machine and the water inlet chamber of the dialyzate system.

The water inlet chamber can furthermore have a level detection and/or an inlet valve. A control of the dialysis machine preferably controls the inlet valve in dependence on the level detection to ensure a desired level in the water inlet chamber. The inlet valve can in particular be arranged downstream of the constant flow regulator. The constant flow regulator and the inlet valve can in particular be arranged in a line which connects the water connection to the water inlet chamber. The inlet valve can be a switching valve. If it is opened, the constant flow regulator in accordance with the invention ensures that the inlet chamber is filled with a reproducible flow.

In accordance with a preferred embodiment of the present invention, the constant flow regulator is configured as a passive flow control element. Sensors and/or control electronics can hereby be dispensed with. The constant flow regulator in particular has a regulation element which is moved against the force of a spring by a differential pressure applied to the constant flow regulator and which changes the flow resistance of the differential pressure regulator. The regulation element can in particular be a plunger which is displaceable into a regulator opening. The regulator opening, the plunger and the spring are preferably configured such that a substantially constant flow through the constant flow regulator independent of the differential pressure is produced within an operation range of differential pressures.

In a preferred embodiment of the present invention, the constant flow regulator used has the following design: the constant flow regulator has a housing which is flowed through by fluid and which has an inlet, a regulator opening and an outlet. A plunger is furthermore provided which is displaceably arranged in the housing, with a regulator passage remaining between the regulator opening and the plunger which is dependent on the relative position between the plunger and the regulator opening and which defines the regulation effect. A spring is furthermore provided against whose force the plunger is displaced by a differential pressure which is applied between the inlet and the outlet of the housing.

The constant flow regulator is preferably configured such as will be described in more detail in the following. The constant flow regulator can in particular be configured in accordance with the second aspect of the present invention.

In accordance with the second aspect of the present invention, which is directed to a constant flow regulator, the present invention comprises in a first variant a constant flow regulator having a housing which is flowed through by fluid and which has an inlet, a regulator opening and an outlet. A plunger is furthermore provided which is displaceably arranged in the housing, with a regulator passage remaining between the regulator opening and the plunger which is dependent on the relative position between the plunger and the regulator opening and which defines the regulation effect. A spring is furthermore provided against whose force the plunger is displaced by a differential pressure which is applied between the inlet and the outlet of the housing. In accordance with the invention, provision is made in accordance with the first variant that the minimal flowed-through cross-section of the regulator passage changes on a displacement of the plunger relative to the regulator opening. In accordance with the invention, the minimal flowed-through cross-section of the regulator passage is thus changed to set the flow resistance of the constant flow regulator in dependence on an applied differential pressure. This in particular enables an improved performance in an operating range having low differential pressures. Higher flow rates are furthermore also hereby possible which enable the use in a dialysis machine.

The constant flow regulator in accordance with the invention is preferably used in a dialysis machine such as was described above in accordance with the first aspect. The constant flow regulator in accordance with the invention is, however, not restricted to the use in a dialysis machine, but can rather, for example, be used in other medical devices.

In a possible embodiment, the length of the regulator passage can be independent of the position of the plunger relative to the regulator opening. The plunger can in particular always completely pass through the regulator opening in this respect. The regulator passage or the regulator opening in this case preferably acts as a diaphragm from a mechanical flow aspect. The regulator opening can in particular be a narrow diaphragm.

Alternatively, the regulator opening and the plunger can be configured such that on a displacement of the plunger relative to the regulator opening, both the length and the minimum flowed-through cross-section of the regulator passage change.

The length of the regulator passage preferably changes in this case in that the plunger is pushed further into the regulator opening as the differential pressure rises so that the length of the regulator opening which is passed through by the plunger changes in dependence on the position of the plunger and thus on the differential pressure. The regulator passage is defined by the region in which the plunger passes through the regulator opening.

The plunger and the regulator opening are preferably configured such that the minimum flowed-through cross-section of the regulator passage decreases as the differential pressure increases. The flow resistance is increased by the reducing cross-section.

Alternatively or additionally, the plunger and the regulator opening can be configured such that the length of the regulator passage increases as the differential pressure increases. The flow resistance is also hereby increased.

The plunger, the regulator opening and the spring are preferably configured such that a flow through the constant flow regulator is produced which is substantially constant and which is independent of the differential pressure within an operating range of possible differential pressures. The spring travel of the spring, the minimum flowed-through cross-section of the regulator passage and, optionally, the length of the regulator passage are coordinated with one another such that the flow resistance of the constant flow regulator tracks the differential pressure such that a substantially constant flow is produced over the total operating range.

The varying minimum flowed-through cross-section of the regulator passage is preferably reached in that the cross-section of the plunger and/or the regulator opening is varied over the range in which the plunger is pushed into the regulator opening on a changing differential pressure.

A plunger is preferably used whose cross-sectional surface and/or diameter varies over the range with which the plunger is displaced relative to the regulator opening with a changing differential pressure.

A plunger is preferably used whose cross-sectional surface and/or diameter reduce(s) progressively, i.e. at an increasing rate, in the flow direction in a first part region. A step region preferably adjoins the first part region in the direction of flow. The first part region and the step region can in particular be arranged at the plunger such that the step region is used in an operating range having lower differential pressures and the first part region is used in an operating range having higher differential pressures.

The inventor of the present invention has recognized that the constant flow regulator becomes more robust with respect to production tolerances or to an initial jamming of the plunger by such a configuration of the plunger, in particular in the range of lower differential pressures.

The first part region having a progressively decreasing cross-section surface and/or diameter in particular allows a particularly effective adaptation to changing differential pressures and thus a high accuracy in the setting of the desired flow. The step region in contrast makes the plunger more robust with respect to production tolerances or mechanical constraints at low differential pressures.

The constant flow regulator is preferably configured such that the first part region is effective in an operating range having higher differential pressures and the step region is effective in an operating range having lower differential pressures, i.e. changes the minimum flowed-through cross-section.

Provision is preferably made that the cross-sectional surface and/or the diameter is reduced in accordance with a theoretically optimum curve in this first part range. The cross-sectional surface and/or the diameter can in particular be reduced such that it theoretically produces a constant flow over the total first part range.

Provision can alternatively or additionally be made that the cross-sectional surface and/or the diameter in the step region deviate(s) from a theoretically optimum curve towards a larger cross-sectional surface and/or larger diameters. In accordance with the invention, no curve progression is thus used in the step region which ensures a constant flow. The inventor of the present invention has, however, recognized that even the smallest differences from the optimum curve actually produce substantial deflections in the behavior of the constant flow regulator in a region having small differential pressures. The inventor has furthermore recognized that differences which produce an increase in the minimum flowed-through cross-section produce greater effects on the flow than differences which produce a decrease in the minimum flowed-through cross-section. The progression of the cross-sectional surface and/or of the diameter therefore deviates in accordance with the invention from the theoretically optimum curve toward a larger cross-sectional surface and/or toward a larger diameter since the constant flow regulator hereby becomes more robust with respect to production tolerances and an initial movement jam.

Provision can alternatively or additionally be made that the step region forms an end region of the plunger. Provision can further alternatively or additionally be made that the cross-sectional surface and/or the diameter of the plunger in the step region reduces at a rate which becomes smaller or which does not reduce at all. While the cross-sectional surface and/or the diameter in the first part region therefore reduces progressively, it reduces degressively or no longer decreases in the step region.

Provision can furthermore be made in accordance with the invention that the first part region ends in an end position of the plunger without differential pressure before the regulator opening and/or before the narrowest part of the regulator opening. The end position of the plunger without differential pressure therefore preferably has no influence on the regulation properties and in particular has no influence on the minimum flowed-through cross-section. The narrowest point of the regulator opening is preferably the point having the smallest cross-sectional surface and/or diameter of the regulator opening.

Provision can furthermore be made in accordance with the invention that the step region in the end position of the plunger without differential pressure extends partially within the regulator opening and partially before the regulator opening and/or at both sides of a narrowest point of the regulator opening. The step region is therefore that region in the end position of the plunger without differential pressure which defines the regulation properties and/or the minimum flowed-through cross-section.

Provision can furthermore be made in accordance with the invention that the length of the step region amounts to less than 50% of the adjustment path of the plunger. The length of the step region preferably amounts to less than 20% of the adjustment path of the plunger. The step region is therefore preferably in particular only used in a small region of low differential pressures.

Provision can furthermore be made that the length of the first part region amounts to more than 50% of the adjustment path of the plunger, preferably more than 80%. The first part region with the progressive reduction of the diameter is thus used over a wide differential pressure range, in particular over such a range with the larger differential pressures.

With a constant flow regulator in accordance with the invention in accordance with the first or second variants, the plunger is preferably pressed by the spring against an abutment on an absence of differential pressure. The abutment thus defines the end position of the plunger without differential pressure.

The stream flow through and/or past the plunger can preferably be blocked in this position. A seal can in particular be provided for this purpose. It provides that small differential pressures can also reliably produce a movement of the plunger and can thus overcome an initial jamming of the plunger since the plunger cannot be flowed around in the end position without differential pressure and therefore first has to be moved against the force of the spring out of the positioning blocking the stream flow.

Such an embodiment is also of advantage independently of the configuration of the constant flow regulator in accordance with the first variant of the second aspect.

The present invention therefore comprises in accordance with a second variant of the second aspect a constant flow regulator for a dialysis machine having a housing which is flowed through by fluid and which has an inlet, a regulator opening and an outlet. A plunger is furthermore provided which is displaceably arranged in the housing, with a regulator passage remaining between the regulator opening and the plunger which is dependent on the relative position between the plunger and the regulator opening and which defines the regulation effect. A spring is furthermore provided against whose force the plunger is displaced by a differential pressure which is applied between the inlet and the outlet of the housing. Provision is made in accordance with the invention that the plunger is pressed against an abutment by the spring on an absence of differential pressure, with the stream flow through and/or past the plunger being blocked in this position. This in particular takes place by a seal. Such an embodiment is not known for constant flow regulators which would be used for dialysis machines.

The blockage of the stream flow through and/or past the plunger preferably takes place in that the abutment has a seal geometry which is pressed against a sealing element arranged at the plunger. The sealing element can in particular be produced from an elastomer material. The sealing geometry can in particular be a sealing edge and/or a sealing bead.

The embodiment in accordance with the second variant can admittedly be used independently of the first variant, but it is preferably used in combination with the features of the first variant.

Preferred embodiments of all variants of the constant flow regulator in accordance with the invention will be shown in more detail in the following.

The plunger and the regulator opening are preferably configured and cooperate such that the regulator passage remains between an outer side of the plunger and an inner side of the regulator opening.

The plunger can be of pin-shaped design in accordance with the invention.

In a possible embodiment, the regulator opening can be of tubular design. In this case, the length of the flow passage is preferably predefined by the length with which the plunger passes through the regulator opening.

In an alternative embodiment, the regulator opening can be designed as a diaphragm, for example as a small narrowing of a flow passage or as the end of a passage tapering in funnel form.

The maximum diameter of the plunger in the region in which it passes through the regulator opening is preferably smaller than the minimum diameter of the regulator opening in this region. In a possible embodiment, the plunger and/or the regulator opening can be rotationally symmetrical. The plunger can optionally, however, also have webs which correspond to the minimum diameter of the regulator opening and which guide the plunger in the regulator opening.

In a possible embodiment of the present invention, the cross-sectional surface and/or the diameter of the tubular regulator opening can be constant. It can in this respect in particular be a cylinder tube.

Alternatively or additionally, the cross-sectional surface and/or the diameter of the tubular regulator opening can increase in the direction of flow in at least one part region. This facilitates the removal of the injection molding tool after the injection procedure.

The cross-sectional surface and/or the diameter of the tubular regulator opening preferably increases by a maximum of 10% over the total extension.

In a possible embodiment, the smallest cross-sectional surface and/or the smallest diameter of the regulator opening can be arranged at the side of the regulator opening facing the inlet.

The tubular restrictor opening can merge at the outlet side without a transition into a fluid line section. The end of the regulator opening is in this case defined by the point up to which the pin is displaced at maximum operating pressure. With a flow passage expanding in the manner of a funnel, only the narrowest point can also form the regulator opening if only this point provides the actually effective regulation.

In a further embodiment of the present invention, the plunger contacts a guide region which is displaceable guided in a guide chamber of the housing. The guide region and the plunger can be produced in one piece. The plunger is preferably guided by the guide section on its movement within the housing.

In a possible embodiment, the guide region can be cylindrical and can be displaceably guided in a cylindrical guide chamber of the housing. The guide region and/or the guide chamber is/are particularly preferably of circular cylindrical form. Other cross-sectional shapes are, however, also conceivable.

The abutment for the plunger against which the latter is pressed by the spring in the state without differential pressure is preferably formed by an end of the guide chamber at the inlet side against which the guide range is pressed by the spring on an absence of differential pressure.

Alternatively or additionally, the guide chamber can have a larger diameter than the regulator opening. The cross-sectional surface and/or the diameter of the guide chamber is/are optionally in particular so large that a fluid passage which has no relevant regulation effect remains between the plunger and the guide chamber.

Further alternatively or additionally, the spring can be arranged in the guide chamber. The spring can in particular extend between an end of the guide chamber at the outlet side and the guide region of the plunger. The spring preferably surrounds the plunger arranged at the guide region.

Further alternatively or additionally, the guide chamber can be arranged between the inlet and the end of the regulator opening at the inlet side.

Further alternatively or additionally, the guide region can have one or more flowed-through openings. The liquid can preferably flow through the plunger without any relative regulation effect.

In accordance with the second variant of the second aspect, the seal can close the fluid flow between the inlet and the one or more flowed-through openings in the position in which the guide region is pressed against the abutment.

The constant flow regulator in accordance with the invention, as shown above, generates a substantially constant flow over its operating range. Substantially constant in the sense of the present invention preferably means that the flow differs by a maximum of 30% from a maximum value, preferably by a maximum of 10%, over the operating range.

The constant flow regulator in accordance with the invention is preferably configured such that it sets a substantially constant flow in its operating range between 500 ml/min and 3000 ml/min, preferably between 1000 ml/min and 1500 ml/min.

Alternatively or additionally, the operating pressure range of the constant flow regulator can comprise differential pressures between 2 bar and 3 bar. The operating pressure range of the constant flow regulator preferably comprises differential pressures between 1 bar and 5 bar, further preferably between 0.5 bar and 5.5 bar. In a preferred embodiment, the operating pressure range of the constant flow regulator comprises differential pressures up to 0.2 bar.

Further alternatively or additionally, the operating pressure range of the constant flow regulator can comprise inlet pressures between 2 bar and 4 bar, preferably between 1.5 bar and 6 bar.

In a possible structural embodiment of the present invention, the housing of the constant flow regulator in accordance with the invention comprises two parts. The parts can in particular be configured as injection molded parts and/or from plastic.

The two parts of the housing are preferably screwed or adhesively bonded to one another. Alternatively or additionally, a first part can comprise a guide chamber, the regulator opening and the outlet. Alternatively or additionally, a second part can comprise the inlet and optionally a sealing structure against which the plunger is pressed by the spring on an absence of differential pressure. The plunger is preferably also produced from plastic and/or as an injection molded part.

The inlet and/or the outlet of the housing can be tubular, with hoses preferably being able to be fastened to the tubular inlet and/or outlet.

BRIEF DESCRIPTION OF THE DRAWINGS

The present invention will now be described in more detail with reference to embodiments and to drawings.

There are shown.

DETAILED DESCRIPTION OF THE PREFERRED EMBODIMENTS

Further scope of applicability of the present invention will become apparent, from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
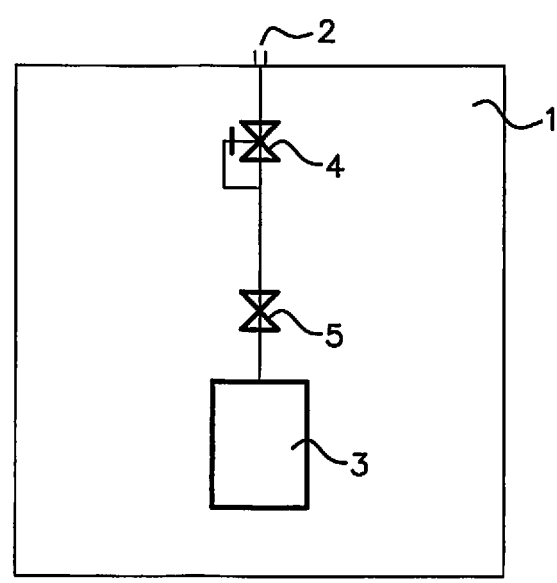
FIG. 1: a dialysis machine in accordance with the prior art.
Figure 2:
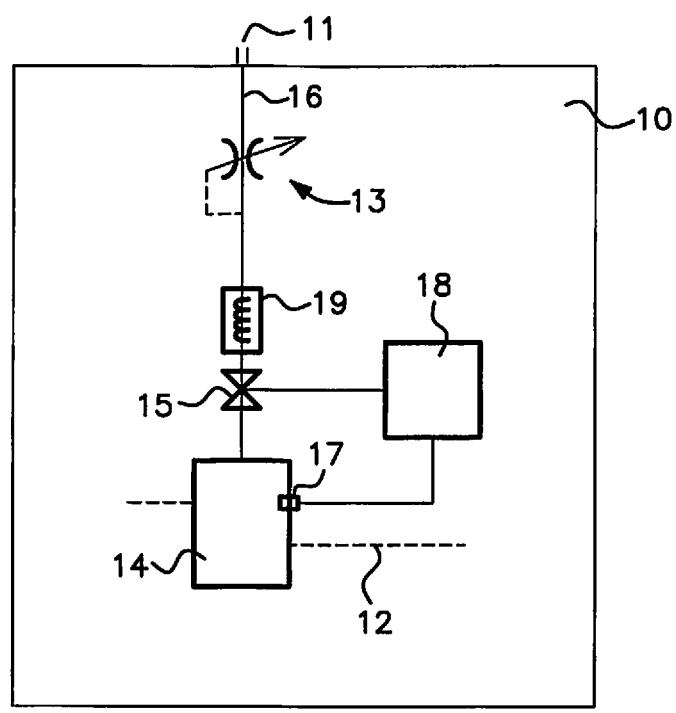
FIG. 2: an embodiment of a dialysis machine in accordance with the invention in accordance with the first aspect of the present invention.

FIG. 2 shows an embodiment of a dialysis machine 10 in accordance with the invention. The dialysis machine has a water inlet 11 with which it can be connected to an external water supply at the installation site. The external water supply can, for example, be an RO ring line, an individual position and/or a reverse osmosis plant. The dialysis machine has a dialyzate system 12 which is only shown schematically in FIG. 2, which has an inlet chamber 14 which can be filled with water via the water inlet 11. For this purpose, the water inlet 11 is connected to the inlet chamber 14 of the dialyzate system 12 via a line 16.

A constant flow regulator 13 is provided in accordance with the invention in the line 16 between the water inlet 11 and the inlet chamber 14 of the dialyzate system. It is designed as a passive flow control element such that it changes its flow resistance in dependence on the pressure difference between the water inlet and the inlet chamber such that an approximately constant flow is adopted over the total operating range. A regulation element is in particular provided which is displaced against the force of a spring by the applied pressure difference between the inlet and the outlet of the constant flow regulator and hereby changes the flow resistance of the constant flow regulator. The regulation element can in particular be a plunger which cooperates with a restrictor opening of the constant flow regulator.

The operating pressure range of the constant flow regulator comprises inlet pressures between 1.5 bar and 6 bar in the embodiment. The constant flow regulator is configured such that it sets a substantially constant flow between 1000 ml/min and 1500 mil/min over the total operating pressure range. A substantially constant flow in the sense of the present invention preferably does not differ from a maximum flow by more than 35%, preferably not by more than 20%.

As further shown in FIG. 2, the inlet chamber 14 of the dialyzate system 12 has a level sensor 17 which is connected to a control 18 of the dialysis machine. An inlet valve 15 is furthermore provided in the line 16 downstream of the constant flow regulator 13. The control controls the inlet valve 15 in dependence on the data of the level sensor 17 to fill the inlet chamber 14. The inlet vale 15 is preferably a switching valve.

A heat exchanger 19 via which the water flowing into the inlet chamber 14 can be heated is furthermore provided in the line 16 downstream of the constant flow regulator 13.

The dialysis machine is preferably a device for hemodialysis and/or hemofiltration. An extracorporeal blood circuit is therefore connectable to the dialysis machine which is typically configured as a disposable. A dialyzer is arranged in the extracorporeal blood circuit which, on the one hand, forms a part of the extracorporeal blood circuit and, on the other hand, is connected to the dialyzate system of the dialysis machine. During a dialysis treatment carried out by the dialysis machine, blood and dialyzate flow through the two halves of the dialyzer which are separated from one another via a membrane in order thus to enable a mass transfer between the dialyzate and the blood. The dialysis machine can in particular have a blood pump and/or a dialyzate pump which is/are controlled by the control 18.

Any desired constant flow regulators can initially be used within the framework of the dialysis machine in accordance with the invention. However, constant flow regulators are preferably used which will be described in more detail in the following.

The constant flow regulators described in the following cannot only be used for dialysis machines, but also in other applications, for example in other medical devices.

Figure 3:
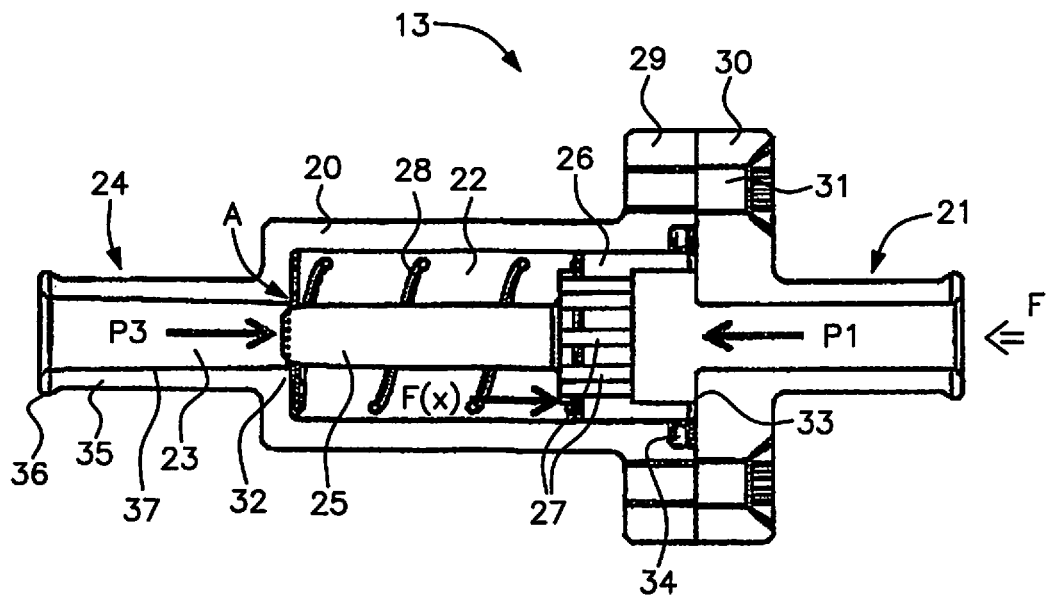
FIG. 3: an embodiment of a constant flow regulator in accordance with the invention in accordance with the first variant of the second aspect of the present invention.

FIG. 3 shows a first embodiment of a constant flow regulator in accordance with the invention. The constant flow regulator comprises a housing 20 having an inlet 21, a guide chamber 22, a regulator opening 23 and an outlet 24. A plunger 25 is displaceably arranged in the housing; it cooperates with the regulation opening 23 and hereby produces the regulation effect of the constant flow regulator.

The inlet 21 and the outlet 24 of the housing are each led out of the housing in tubular form so that a respective hose nozzle can be pushed onto the inlet 21 and onto the outlet 24. The inlet 21 and the outlet 24 have a smaller outer diameter for this purpose than the middle part of the housing. The outer surfaces of the tubular section forming the inlet 21 and the outlet 24 each have a cylindrical section 35 to which a clip can be attached and also each have a bead 36 which prevents a removal of the hose nozzle after the attachment of the clip.

The plunger is arranged at a guide region 26 which is displace ably guided in the guide chamber 22. The guide region has a cylindrical outer contour which contacts the likewise cylindrical inner contour of the guide chamber 22 and is guided at it.

The regulator opening is formed by a tubular section 37 of the housing which adjoins the guide chamber 22 and which has a smaller diameter than the guide chamber itself and/or is formed by the narrowest point 32 of this section. The plunger 25 is of pin shape and extends axially from the guide region 26 to the regulator opening. Depending on the position of the guide region 26, the plunger is pushed into the tubular section 37 by different amounts or is moved by different amounts relative to its narrowest point. A regulator passage which is depending on the relative position between the plunger and the regulator opening and which defines the regulation effect is hereby produced between the inner contour of the regulator opening 23 or 32 and the outer contour of the plunger element 25.

A spring 28 is arranged in the guide chamber 22; it extends between the end of the guide chamber 22 at the outlet side and the end of the guide region 26 at the outlet side and preloads the plunger against the direction of flow.

The guide region 26 in the embodiment has a plurality of passage bores 27 through which liquid can flow substantially without any regulation effect. The guide chamber itself has no relevant regulation effect due to the increased cross-section of the guide chamber 22. The flow resistance of the regulator is therefore defined by the regulator passage remaining between the regulator opening 23 or 32 and the plunger 25.

The housing 20 in the embodiment is made up of two elements 29 and 30. The element 29 comprises the outlet 24, the regulator guide 23 or 32 and the guide chamber 22. The second element comprises the inlet 21 as well as an abutment region 33 against which the guide region 26 of the plunger is pressed by the force of the spring 28 in the case of an absence of differential pressure. Both housing elements each have a flange region in which they are screwed together by screws 31. In this respect, a sealing element 34, a sealing ring in the embodiment, is provided which seals the two housing elements with respect to one another. The housing elements and the plunger are preferably designed as injection molded plastic parts. The first housing element 29 is preferably produced from a translucent and/or transparent material to be able also to visually check the function of the constant flow regulator.

In the embodiment, the regulator passage is configured as an annular gap which extends between the outer periphery of the plunger and the inner periphery of the regulator opening. In the embodiment, the regulator opening and the plunger have a rotationally symmetrical contour and are arranged coaxially.

The regulator opening 23 can have a constant diameter in a possible embodiment.

In the embodiment, the diameter of the tubular section comprising the regulator opening in contrast expands in funnel-like shape in the direction of flow. The expansion is, however, only slight, with the expansion of the cross-sectional surface of the tubular section in the embodiment amounting to a maximum of 10% over the total movement range of the plunger starting from the narrowest point 32. In the embodiment, the section 23 comprising the regulator opening merges directly into the outlet 24 of the constant flow regulator.

The narrowest point 32, i.e. the point with the smallest cross-sectional surface or the smallest diameter of the regulator opening 23 is provided at the side of the regulator opening 23 at the inlet side in the embodiment. This point therefore defines together with the diameter of the plunger 25 at this point the minimally flowed-through cross-section of the regulator passage. Despite the only small expansion of the passage, the actually effective regulation arises in a possible embodiment essentially only at this narrowest point 32 so that only it acts as a regulator opening.

In this respect, the cross-sectional surface or the diameter of the plunger changes in the region which is led past the narrowest point 32 on a movement of the plunger. The cross-sectional surface or the diameter of the plunger in particular reduces in the direction of flow in this respect. The minimum flowed-through cross-section of the regulator passage remaining between the plunger 25 and the regulator opening 23 hereby depends on the relative position between the plunger 25 and the regulator opening 23.

In accordance with the invention, the plunger 25 is displaced against the force of the spring 28 in the direction of flow by a pressure difference between the inlet 21 and the outlet 24. The minimum flowed-through cross-section of the regulation passage remaining between the plunger 25 and the regulator opening 23 is hereby changed. In a possible embodiment, the length of the regulator passage can also vary and can likewise be used for influencing the flow. The change in the cross-section and, optionally, in the length takes place such that an approximately constant flow results.

In the embodiment shown in FIG. 3, the tip of the plunger is in the region of the narrowest point 32 of the regulator opening in the situation of the constant flow regulator shown in FIG. 3 without differential pressure. In this starting position, the very short regulator passage remaining between the tip of the plunger and the narrowest point of the regulator opening behaves as an annular gap diaphragm. The flow amount is determined by the orifice area A of the regulator passage, i.e. by the minimally flowed-through cross-section of the regulator passage.

The constant flow regulator in accordance with the invention is designed such that the minimum flowed-through cross-section and thus the orifice area A of the regulator passage vary in dependence on the pressure difference. It is effected by a corresponding shape of the plunger.

Figure 4:
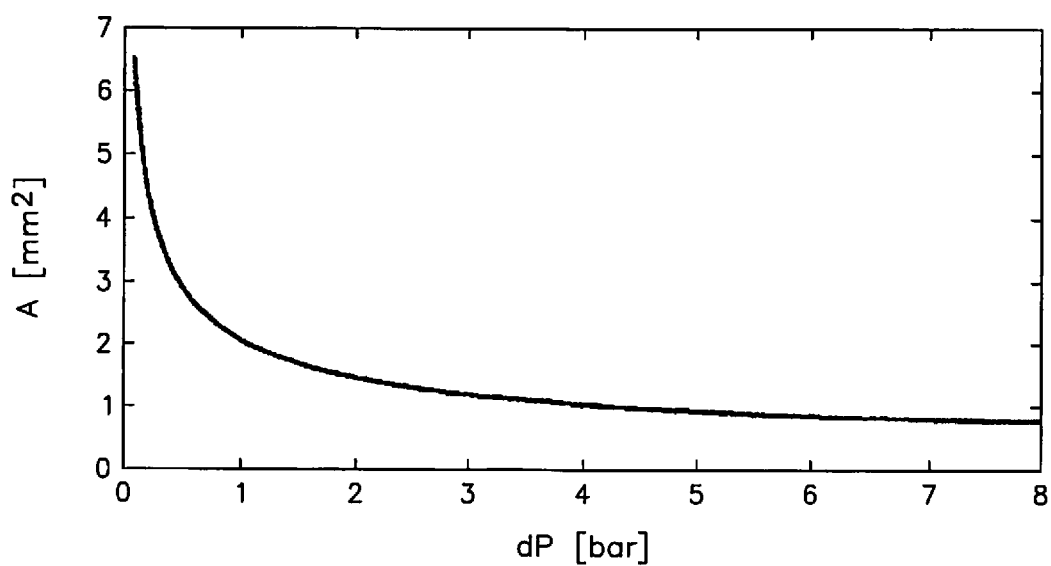
FIG. 4: a diagram which shows the minimum flowed-through cross-section of the regulator passage in dependence on a differential pressure in the embodiment shown in FIG. 3.

The minimally flowed-through cross-section of the regulator passage in the embodiment shown in FIG. 3 is shown in dependence on the differential pressure in FIG. 4. As can immediately be seen from FIG. 4, the highest changes of the cross-sectional surface occur at low differential pressures.

Since low pressure differences can occur over the constant flow regulator despite a sufficient inlet pressure by flow resistances downstream of the constant flow regulator such as a heat exchanger, this operation region is actually also relevant on a use in a dialysis machine.

The relationship shown in FIG. 4 between the cross-sectional surface of the constant flow regulator and the differential pressure requires a shape of the plunger in which the diameter of the plunger progressively reduces in the direction of flow or in the direction of movement of the plunger as the differential pressure increases. This means that the diameter reduces, and indeed at a rate increasing in the direction of flow.

The relationships can be derived as follows from the orifice formula. In accordance with the orifice formula, the following relationship results between the flow Q which is to be set to a constant value and the orifice area A of the diaphragm, the differential pressure $\Delta P$ between the inlet pressure P1 and the outlet pressure P3 (i.e. $\Delta P = P1 - P3$) and the viscosity $\rho$ and a coefficient $\alpha$:

$$Q = \alpha A \sqrt{\frac{2}{\rho}(\Delta P)} = const.$$

The resulting orifice area A in dependence on the differential pressure $\Delta P$ is obtained from the conversion of the formula:

$$A = \frac{Q}{\alpha\sqrt{\frac{2}{\rho}(\Delta P)}}$$

The differential pressure acts on the cross-sectional surface of the plunger in the orifice area of the constant flow regulator, i.e. in the embodiment shown in FIG. 3 in the region of the narrowest point 32 of the regulator opening. The plunger is moved so far in dependence on the differential pressure until the spring force and the force effect produced by the differential pressure on the plunger are in equilibrium. The position x of the plunger therefore depends as follows on the spring stiffness R and on the cross-sectional surface A of the plunger in the orifice area:

$$x = \frac{F}{R} = \frac{\Delta P * A_i}{R}$$

Figure 5:
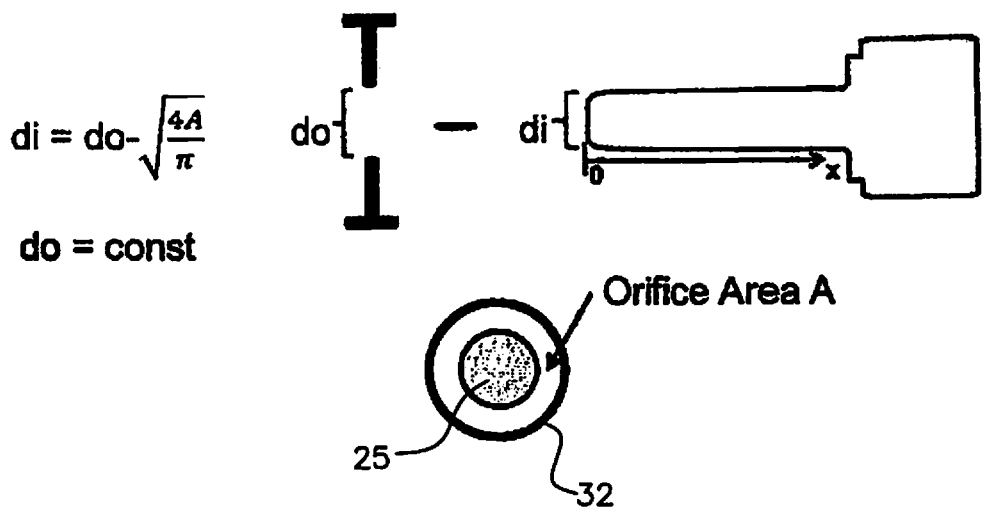
FIG. 5: a schematic representation for illustrating the minimum flowed-through cross-section of the regulator passage in accordance with the invention changed a displacement of the plunger relative to the plunger opening.

As shown schematically in FIG. 5, the orifice area A is the remaining area of the regulator opening which is not blocked by the plunger. In this respect $A_0$ is the minimal cross-sectional surface of the regulator opening defined by the minimal diameter $d_0$ and $A_i$ is the cross-sectional surface of the plunger in the region of the narrowest point 32 given by the diameter $d_1$ of the plunger at the position x.

The diameter of the plunger $d_1$ at the position x is therefore given by the difference from the constant outer diameter do of the narrowest point of the regulator opening which is predefined by the housing and the diaphragm area required in accordance with the above formula. In this respect, the following applies to the orifice area A which is used in formulas 1 and 2:

$$A = A_0 - A_i = \frac{\pi}{4}(d_0^2 - d_i^2)$$

The following dependence of the diameter $d_i$ of the plunger on the position x hereby results:

$$d_i(x) = \sqrt{\frac{4A_0}{\pi} + \frac{Q^2\rho}{2\alpha^2\pi Rx} - \frac{2Q}{\alpha\sqrt{\frac{8\pi Rx}{\rho}}}}$$

Since the force acting on the surface $A_i$ through the differential pressure $\Delta P$ is in a linear relationship with the position x, a curve is essentially produced for the progression of the diameter $d_i$ in dependence on the position x which corresponds to the inverse progression of the orifice area A shown in FIG. 4. The diaphragm surface thus changes to a very high degree over the first millimeters. This initial region corresponds to the operating point at small differential pressure.

Figure 6:
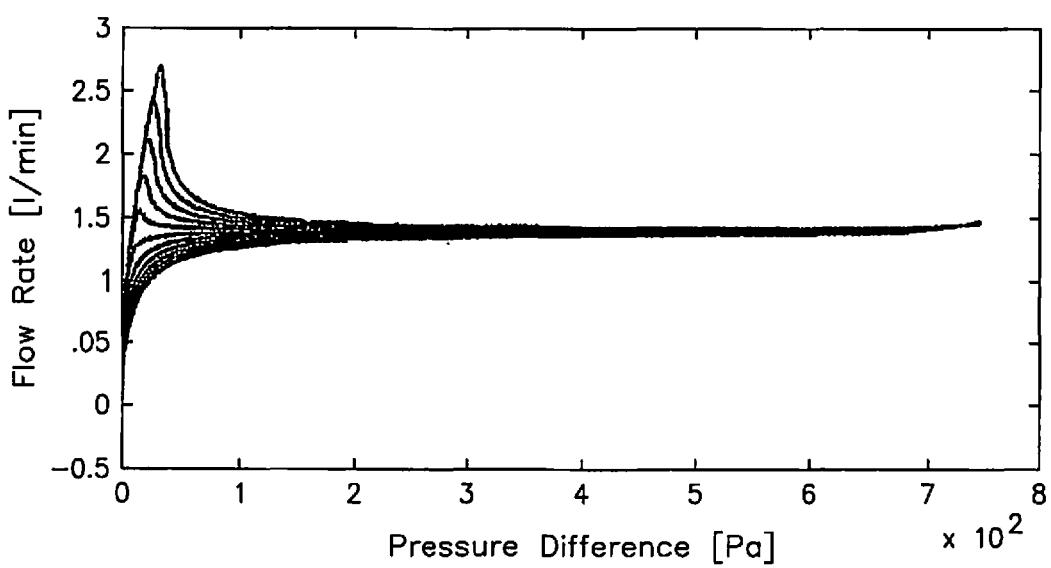
FIG. 6: a diagram which shows the influence of differences of the plunger geometry from an optimum desired geometry on the flow through the constant flow regulator in the embodiment shown in FIGS. 3 and 4.

The inventor of the present invention has now recognized that tolerances of the plunger diameter and of the spring length can produce large deviations of the flow in this critical region. Flows which are too high in particular arise in the low differential pressure range when the plunger surface is too low due to production tolerances or when the plunger covers too small a distance due, for example, to sticking friction and/or to a spring which is too stiff or too long. FIG. 6 shows a simulation result which represents the deviation from a desired flow in dependence on tolerances.

It can be seen in FIG. 6 that with tolerances in the direction of too large a diaphragm surface the deviation in the flow is substantially more dramatic than with the same tolerances in the direction of too small a flow.

Figure 7:
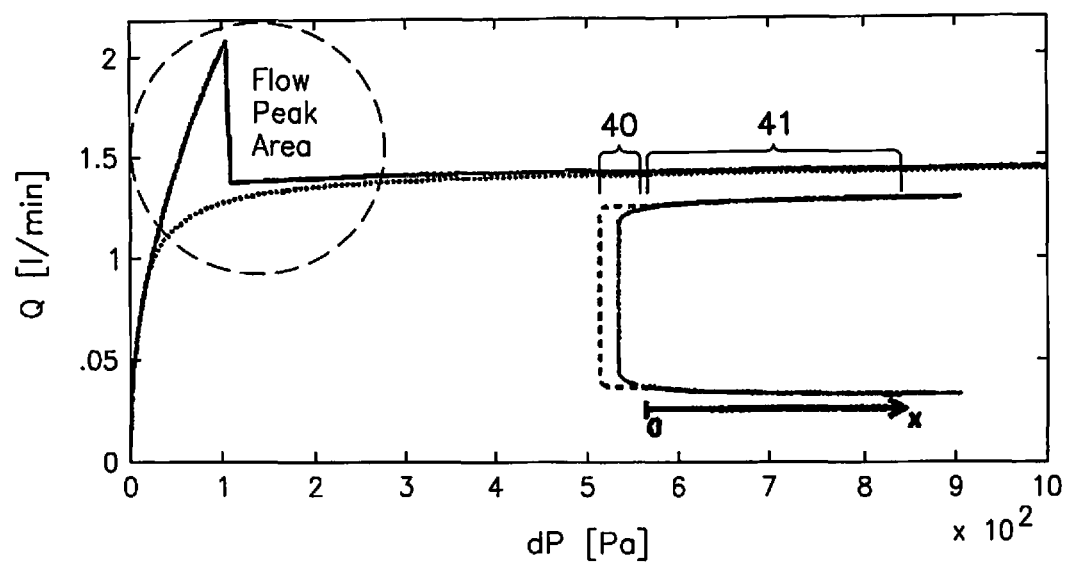
FIG. 7: the shape of a plunger for the constant flow regulator in accordance with a preferred embodiment of the first variant of the second aspect of the present invention together with a schematic representation of the flow produced hereby in dependence on the differential pressure.
Figure 8:
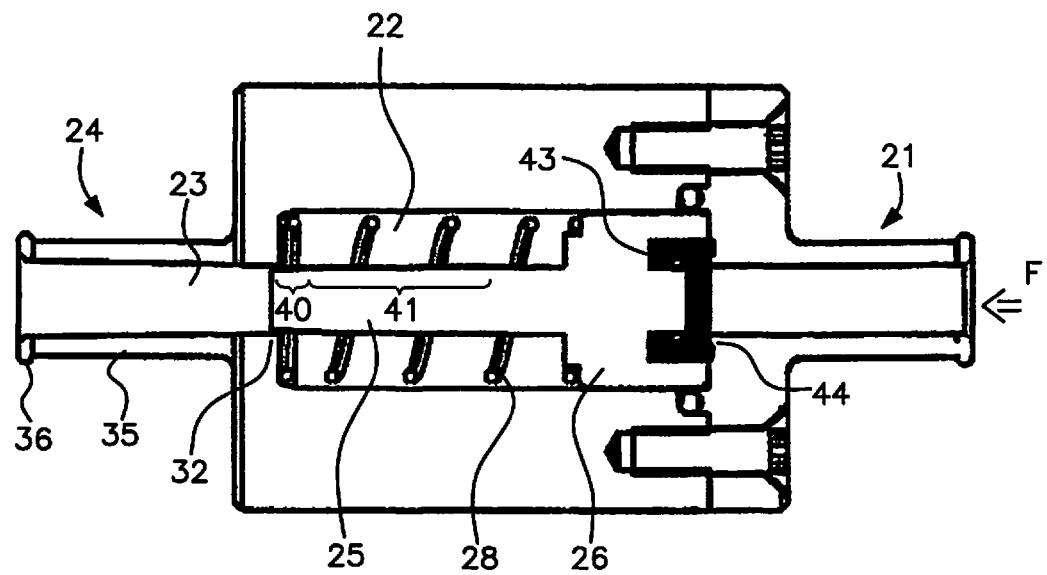
FIG. 8: a further embodiment of a constant flow regulator in accordance with the invention in which the first and second variants of the second aspect are implemented in combination.

In the further embodiments of a constant flow regulator in accordance with the invention shown in FIGS. 7 and 8, measures have therefore been taken to reduce such great deviations in the direction of high flows and thus to make the constant flow regulator more robust with respect to production tolerances and factors of influence such as sticking friction, etc.

FIG. 7 shows an alternative geometry for the plunger tip. In this respect, the geometry of the plunger differs from the above-described ideal line of the orifice equation in the region of the tip, and indeed in the direction toward larger diameters. For this purpose, instead of the great reduction in the diameter at the position x=0, i.e. at that point which is arranged in the position without differential pressure in the region of the narrowest point 32 of the regulator passage, a step 40 is provided construction-wise which prevents the diameter $d_i$ from falling below a certain value. The diagram in FIG. 5 shows in an exaggerated manner the effect of this step or edge on the flow. A region 41 in which the diameter $d_i$ follows the ideal line and thus progressively decreases in the direction of flow, i.e. against the arrow indicating the position x, then adjoins the step region 40. Conversely, the diameter $d_i$ increases degressively in the region 41 in dependence on the position x. The region with the greatest change of the diameter $d_i$ is therefore that one which directly adjoins the step region 40.

In the embodiments shown, the position x defines that position of the plunger which is located in the region of the point 32 having the narrowest diameter of the regulator opening. The above-named relationships can, however, alternatively also be defined in relation to the inlet of the regulator opening. This is in particular the case when the regulator opening has a constant diameter.

Furthermore, as shown in FIG. 8, the risk of an absent deflection due to sticking friction or too stiff/long a spring is prevented construction-wise. For this purpose, the plunger has a seal at the rear side of the guide element 26 which is pressed against the end of the guide chamber at the inlet side by the spring in the position without differential pressure, with the seal being able to comprise an elastomer, for example. The end of the guide chamber at the inlet side is equipped with a sealing geometry 44, in the embodiment with a sealing bead surrounding the inlet 21 and which is pressed against the seal 43 at the plunger. A flowing through of the flow bores 27 of the guide region 26 is hereby prevented in the position without differential pressure and equally a flowing around of the guide region. This arrangement has the result that the plunger has to be moved to release the flow path. It is hereby ensured that small pressure differences are sufficient to overcome the sticking friction. It is a further advantage of this arrangement that the constant flow regulator has been supplemented by a non-return function.

The dialysis machine in accordance with the present invention has the advantage that the feed flow of water into the dialysis system of the machine is regulated automatically. A manual setting of the pressure as currently on the putting into operation is thus no longer necessary. Furthermore, an inexpensive and simple design is ensured. In this respect, the constant flow regulator is a passive component which is service-free.

The constant flow regulators in accordance with the invention in accordance with the second aspect of the present invention are optimized for low differential pressures and high flow precision. The second variant furthermore has an integrated check valve function.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A dialysis machine, comprising,
wherein the dialysis machine is configured to be used for at least one of hemodialysis and hemofiltration: a dialyzate system having a water inlet chamber; a water inlet via which the dialyzate system can be connected to an external water supply providing ultra-pure water; a constant flow regulator provided between the water inlet and the water inlet chamber of the dialyzate system; and said water inlet chamber including a level detection and an inlet valve, with a control of the dialysis machine controlling the inlet valve in dependence on the level detection, said constant flow regulator being configured as a passive flow control element and arranged to provide a substantially constant flow into the water inlet chamber when the inlet valve is open, said constant flow regulator having a flow resistance that changes in dependence on an applied pressure difference such that the substantially constant flow is independent of said pressure difference and results over a predefined operating range.

2. The dialysis machine in accordance with claim 1, wherein the constant flow regulator comprises:
a housing which is flowed through by fluid and which has an inlet, a regulator opening and an outlet;
a plunger which is displaceably arranged in the housing, with a regulator passage remaining between the regulator opening and the plunger which is dependent on a relative position between the plunger and the regulator opening and which defines a regulation effect; and
a spring against whose force the plunger is displaced by a differential pressure between the inlet and the outlet of the housing.

3. The dialysis machine of claim 2, wherein a minimum flowed-through cross-section of the regulator passage changes on a displacement of the plunger relative to the regulator opening.

4. The dialysis machine of claim 3, wherein both a length of the regulator passage and the minimum flowed-through cross-section of the regulator passage changes on the displacement of the plunger relative to the regulator opening.

5. The dialysis machine of claim 3, wherein at least one of the minimum flowed-through cross-section of the regulator passage reduces as the differential pressure increases, and a length of the regulator passage increases as the differential pressure rises.

6. The dialysis machine of claim 3, wherein at least one of a cross-sectional surface and a diameter of the plunger reduces progressively, i.e. at an increasing rate, in a direction of flow in a first part region, with a step region adjoining the first part region in the direction of flow.

7. The dialysis machine of claim 6, wherein the diameter of the plunger reduces at a rate which becomes smaller or does not reduce at all in the step region.

8. The dialysis machine of claim 6, further comprising at least one of:
the first part region ends before the regulator opening in an end position of the plunger without differential pressure;
the first part region ends before a narrowest point of the regulator opening in an end position of the plunger without differential pressure;
the step region extends partly within the regulator opening and partly before the regulator opening in an end position of the plunger without differential pressure; and
the step region extends at both sides of the narrowest point of the regulator opening in an end position of the plunger without differential pressure.

9. The dialysis machine of claim 3, wherein the plunger is pressed against an abutment by the spring on an absence of differential pressure, with a flow through or past the plunger being blocked in this position.

10. The dialysis machine of claim 9, wherein the flow through or past the plunger is blocked by a seal.

11. The dialysis machine of claim 2, wherein the regulator opening is tubular, with at least one of a cross-sectional surface and a diameter of the tubular regulator opening increasing in a part region in a direction of flow, and with at least one of a smallest cross-sectional surface and a smallest diameter being arranged at a side of the regulator opening facing the inlet.

12. The dialysis machine of claim 2, wherein the plunger is connected to a guide region which contacts an inner wall of a guide chamber of the housing and is slidingly guided in the guide chamber on the inner wall.

13. The dialysis machine of claim 1, wherein the constant flow regulator has a substantially constant flow between 500 ml/min and 3000 ml/min.

14. The dialysis machine of claim 2, wherein the housing comprises a first part and a second part which are screwed or adhesively bonded to one another, said first part including a guide chamber, the regulator opening and the outlet; and the second part including the inlet.

15. The dialysis machine of claim 14, wherein the second part includes a sealing structure against which the plunger is pressed by the spring on an absence of differential pressure.

16. The dialysis machine of claim 6, wherein a length of the step regions amounts to less than 50% of an adjustment path of the plunger and a length of the first part region amounts to more than 50% of the adjustment path of the plunger.

17. The dialysis machine of claim 12, wherein an abutment for the plunger is formed by an end of the guide chamber at an inlet side against which the guide region is pressed on an absence of differential pressure, with the guide chamber having a larger diameter than the regulator opening.

18. The dialysis machine of claim 1, wherein an operating pressure range of the constant flow regulator includes at least one of differential pressures between 0.5 bar and 5.5 bar, and inlet pressures between 1.5 bar and 6 bar.

* * * * *